United States Patent [19]

Cooke et al.

[11] Patent Number: 5,670,150
[45] Date of Patent: Sep. 23, 1997

[54] NON-DEPLETING CD4-SPECIFIC MONOCLONAL ANTIBODIES FOR THE TREATMENT OF INSULIN-DEPENDENT DIABETES MELLITUS (IDDM)

[75] Inventors: Anne Cooke; Herman Waldmann, both of Cambridge, United Kingdom

[73] Assignees: University College London, London; Glaxo Wellcome P.L.C., Middlesex, both of United Kingdom

[21] Appl. No.: 436,843

[22] Filed: May 8, 1995

Related U.S. Application Data

[63] Continuation of Ser. No. 90,203, Dec. 1, 1993, abandoned.

[30] Foreign Application Priority Data

Jan. 14, 1991 [GB] United Kingdom .................. 9100741

[51] Int. Cl.$^6$ .................. A61K 39/395; C07K 16/18; C07K 16/24; C07K 16/26

[52] U.S. Cl. .................. 424/154.1; 424/145.1; 424/158.1; 424/143.1; 530/388.75; 530/388.24

[58] Field of Search .................. 424/145.1, 154.1, 424/158.1, 143.1; 530/388.24, 388.75; 514/7

[56] References Cited

PUBLICATIONS

Waldmann, Herman, Immunology Today, 14(6):247–251, 1993.
Waldmann, T.A, Science, 252: 1657–1662, Jun. 1991.
Varey, A.M et al., (Autoimmunity), Biochem Soc. Transactions, 19:187–191.
Shizuru, J.A. et al., Science, 240: 659–662, 29 Apr. 1988.
Charlton, B. et al., Autoimmunity ) 4:1–7, 1989.

*Primary Examiner*—Susan A. Loring

[57] ABSTRACT

Non-depleting CD4 monoclonal antibodies may be used in the treatment of insulin-dependent diabetes mellitus.

9 Claims, No Drawings

NON-DEPLETING CD4-SPECIFIC MONOCLONAL ANTIBODIES FOR THE TREATMENT OF INSULIN-DEPENDENT DIABETES MELLITUS (IDDM)

This is a continuation of application Ser. No. 08/090,203, filed on Dec. 1, 1993, which was abandoned upon the filing hereof.

The present invention relates to the use of certain antibodies in the prevention and treatment of insulin-dependant diabetes mellitus.

Insulin-dependant diabetes mellitus (hereafter IDDM) is the juvenile-onset form of diabetes. At present there is no available cure for the disease and treatment consists of maintenance of insulin levels by oral or intramuscular administration and palliation of the inevitable side-effects both of the disease itself and of the treatments.

There has been a continuing need to find a means to arrest the loss of insulin-producing β-cells in the pancreas which is the immediate result of the underlying abnormalities, but little progress has been made.

The present invention is founded upon the surprising observation that administration of a non-depleting CD4 monoclonal antibody (hereafter nd CD4 mAb) can arrest the loss of insulin-producing cells in an animal model of IDDM. It is now believed that the use of nd CD4 mAbs will be effective in arresting IDDM in humans and that this treatment will also permit regeneration of the β-cells such that the course of the disease may even be reversed.

WO-A-90/15152 describes the use of nd CD4 mAbs in conjunction with non-depleting CD8 monoclonal antibodies in inducing tolerance to an antigen and suggests that this may be useful in surgery and therapy, for instance in preventing transplant rejection, treating autoimmune diseases and in avoiding undesirable immune reactions to peptide and hormone therapeutic agents. However this treatment is intended to block $CD4^+$ and $CD8^+$ cells and there is no indication that nd CD4 mAbs alone would be useful in any treatment.

Accordingly the present invention provides a method for treating insulin-dependant diabetes mellitus comprising administering an effective, non-toxic amount of at least one non-depleting CD4 monoclonal antibody to a human or non-human patient in need thereof.

As used herein the term "antibody" is intended to include any binding member having a binding domain which reacts with an epitope of the CD4 cell surface antigen. Thus the invention also covers derivatives and homologues of CD4 antibodies, fragments of antibodies containing at least one antigen binding site such as Fab and F(ab')2 fragments and "single domain antibodies" also known as dabs. Monoclonal antibodies according to the invention are antibodies or fragments thereof produced by a clone of cells all derived from a single antibody-producing cell, which may have been obtained from a mammal immunised against the antigen recognised by the antibody or by transformation of a cell with expressible DNA encoding the antibody or fragment thereof, such DNA having been removed from a cell obtained from a mammal immunised against the antigen recognised by the antibody or constructed by recombinant techniques. Techniques of recombinant DNA technology may be used to produce antibodies or chimeric molecules with appropriate specificity for CD4. Such techniques may involve introducing DNA encoding an immunoglobulin variable region, or one or more complementarity determining regions capable of binding CD4, to the constant regions, or constant regions plus framework regions, of a different immunoglobin, for example to convert a mouse-derived monoclonal antibody into one having largely human immunoglobulin characteristics (see EP 184187A, GB 2188638A). Another possibility is to attach just the variable region of an antibody to another non-immunoglobulin molecule, to produce a chimeric molecule (see WO 86/01533). Yet another possibility would be to produce a mutation in the DNA encoding the monoclonal antibody, so as to alter certain of its characteristics without changing its essential specificity. This can be done by site-directed mutagenesis or other techniques known in the art. Monoclonal antibodies and derivatives and homologues thereof and fragments thereof are produced by conventional techniques.

As used herein the term "CD4 monoclonal antibody" refers to a monoclonal antibody, or fragment thereof containing at least one antigen-binding site, capable of specifically binding an epitope of a CD4 cell surface antigen. The term "CD4 cell surface antigen" includes the human CD4 cell surface antigen and corresponding cell surface antigens of other mammals such as the L3T4 antigen of mice.

As used herein the term "non-depleting CD4 monoclonal antibody" refers to CD4 monoclonal antibodies which deplete fewer than 50% of target cells in vitro. Preferred nd CD4 mAbs deplete fewer than 25% and most probably less than 10% of target cells in vitro.

A simple test to ascertain wherein a CD4 mAb should be regarded as non-depleting is to take a sample of peripheral blood, count the target cells, ie $CD4^+$ cells, in an aliquot as a control, treat a further aliquot with the CD4 mAb and count the target cells after treatment; if there are 50% or greater target cells in the treated aliquot compared with the control aliquot, the CD4 mAb is non-depleting in accordance with the invention.

For use in the present invention nd CD4 mAbs may be obtained by conventional techniques for raising mAbs against CD4 and screening and selecting clones with secrete non-depleting antibodies. Typically such antibodies will be of the $IgG_2$ class such as rat $IgG_{2a}$, mouse $IgG_{2b}$ or human $IgG_2$ but human $IgG_4$ are also useful. A preferred nd CD4 mAb for use in accordance with the present invention is YTS177.9 produced by a hybridoma deposited with the European Collection of Animal Cell Cultures Vaccine Research and Production Laboratory, Public Health Laboratory Service, Centre for Applied Microbiology and Research, Porton Down, Salsibury, Wiltshire SP4 OJG, United Kingdom under accession number ECACC 90053005 on 30th May 1990 in connection with International patent Application No PCT/GB90/00840.

Other preferred nd CD4 mAbs for use in the present invention include nd CD4 mAb fragments of YTS 177.9 (ECACC 90053005) and nd CD4 mAbs and fragments thereof which have similar or higher affinity for the same epitope as YTS 177.9.

The treatment of diabetes patients in accordance with the present invention may commence in individuals identified as being at risk (for instance because of a family history of IDDM) prior to emergence of the disease but this is generally less preferred as it is believed that this will lead to a generalised tolerising of the patient to irrelevant antigens leading to a state of immunosuppression. More preferably the treatment is commenced once the disease has become patent since at this stage loss of β-cells has already commenced and the treatment will then primarily interfere with the cause of the disease. Ideally treatment will be commenced soon after the disease has become patent so that the patient will retain the majority of β-cells and, even if there is no regeneration of β-cells, insulin levels will be susceptible of management by conventional techniques but avoiding administration of insulin. Even when the disease has progressed to a late stage, the treatment will be beneficial in protecting the patient's remaining β-cells.

Treatment according to the invention comprises administration of at least one dose of nd CD4 mAb and preferably comprises a course of several doses. The exact amount to be administered in any single dose and the number and timing of any subsequent doses will be determined by many factors including the age, sex, weight and size of the patient, the patient's general health and level of nutrition and the stage to which the patient's disease has progressed. As a general guide, it is believed that saturating amounts of the nd CD4 mAb will be most effective and that such amounts may be determined by routine pharmacokinetic studies; administration of greater than such amounts is uneconomic but unlikely to be harmful whereas administration of less than saturating amounts may also be effective but is likely to be less effective such that additional doses may be required.

In a model mouse system, doses of from 1 μg to 2 mg, preferably from 400 μg to 1 mg of nd CD4 mAb are administered. In humans, doses of from 1 to 400 mg, such as from 3 to 30 mg, for example from 5 to 20 mg of nd CD4 mAb may be contemplated in an otherwise normal healthy adult of about 75 kg.

Typical treatment regimes involve repeat doses being administered several times per week, for instance from 1 to 7 times per week, preferably from 1 to 4 times per week, for example 3 times per week and such regimes may continue for several weeks or even months, for instance for at least 2 weeks and up to 6 months, more preferably up to two months. It is presently envisaged that a single course of treatment will cure the disease for the lifetime of the patient but relapses and recurrences of the disease may be treated with further courses of treatment.

Preferably the nd CD4 mAbs are administered in accordance with the invention by conventional routes such as orally or parenterally, for instance by subcutaneous or intravascular, preferably intravenous, injection. Where large doses are to be administered or the chosen route of administration limits the amount that may be delivered to a patient in a single injection, several sub-doses may be administered to achieve the desired total dose or the dose may be infused for instance intravenously.

Conveniently the nd CD4 mAbs are administered in the form of a composition comprising a pharmaceutically acceptable diluent or carrier. Preferred compositions are pharmaceutical formulations for oral administration or for injection. Such formulations will generally comprise, in addition to a conventional diluent or carrier, suitable accessory ingredients. For oral administration the formulations may be presented in the form of tablets, capsules and other discrete dosage units or in multi-dose form such as bulk powders and liquids. For parental administration the formulations may be presented as solutions for injection, concentrated solutions to be diluted with a solvent for instance with pyrogen-free demineralised water or water for injection) prior to injection or as dry powders for dissolution in a solvent (for instance water for injection) prior to injection. The accessory ingredients, which will be selected according to the type of presentation, may be fillers, flavours, tabletting aids and coatings, preservatives, antioxidants, stabilisers, buffers, antimicrobial agents, surfactants, salts for adjusting tonicity and other conventional ingredients well known in the art of pharmacy.

As previously mentioned, it is sufficient for the present treatment to administer a single nd CD4 mAb species. Use of a cocktail of nd CD4 mAbs may also be contemplated but the use of CD8 mAbs and depleting mAbs is not required and preferably is avoided. In a particular aspect the invention therefore provides a method as hereinbefore described consisting essentially of administering a single nd CD4 mAb species or a composition thereof. Preferably the method consists of the administration of a composition of a single nd CD4 mAb species unaccompanied by administration of any CD8 mAb and unaccompanied by administration of any depleting mAb.

In a further aspect the present invention provides the use of and CD4 mAb in the preparation of a medicament for use in the treatment of IDDM in a human or non-human. Preferably the medicament is a composition or pharmaceutical formulation as hereinbefore described. The treatment will be as hereinbefore described, preferably using nd CD4 mAb YTS 177.9

The invention will now be illustrated by the following Example which is not intended to limit the scope of protection in any way.

EXAMPLE 1

The NOD mouse is considered by many to be a good model for IDDM since the spontaneous incidence among females is 60 to 80% by 30 weeks in most colonies. Among males, the incidence is much lower (for instance less than 10%) and this makes them an ideal recipient, when immunocompromised by irradiation, in which to induce disease by the transfer of spleen cells from diabetic donors.

In this study it is shown that YTS177 strongly protects NOD mice from IDDM transferred by diabetic donor spleen cells. YTS177 is a non-depleting $IgG_{2a}$ anti-CD4 rat monoclonal antibody which although recognising the same epitope as the depleting $IgG_{2b}$ monoclonal anti-CD4 YTS191.1 (ECACC 87072282) has a different mode of action since $CD4^+$ T cells are not eliminated but appear to be permanently anergised.

Groups of 4 or 5 mice were irradiated using a cobalt source (650 rads per mouse) and spleen cells ($2 \times 10^7$ per mouse) from diabetic donors were transferred intravenously the following day. A control group (Group 1) received no antibody treatment. Two groups of mice were treated with YTS177, given i.v. (2 mg per mouse) 3 days before transfer of spleen cells, and i.p. (2 mg per mouse on each occasion) on the next 2 days and then the same dose i.p. 3 times weekly for a total of 10 days following transfer of spleen cells (Group 3) or until sacrifice at week 4 (Group 2). The experiment was repeated for groups 1 and 2 only.

As can be seen from Table 1 (Experiments 1 and 2) below, none of the mice in Groups 1 and 2 were hyperglycaemic by week 4 compared with 7/9 control animals. Three months later all mice in Group 3 were still normoglycaemic.

In addition to repeating Groups 1 and 2, Experiment 2 included a group of mice in which YTS177 treatment was delayed until 12 days after transfer of spleen cells when it was given i.v., i.p. and i.p. on 3 consecutive days and then 3 times weekly as before (Group 4). In Experiments 3 and 4 Groups 1 and 4 were repeated and administration of the depleting CD8 mAb (YTS169.4; ECACC 87072284) to a further group of mice (400 μg i.v., i.p. and i.p. on 3 consecutive days) starting 12 days after transfer of spleen cells was included for comparison (Group 5). Table 1 shows that no animal in Experiments 2,3 or 4 given YTS177 became diabetic whereas 9/13 untreated animals and 1/10 animals treated with depleting CD8 mAb were hyperglycaemic by week 5. In Experiment 4, a further group of mice (Group 6) were given the depleting CD4 mAb (YTS191.1 ECACC 87072282) starting 12 days after transfer and any protection conferred on these animals was barely significant.

The doses of the depleting antibodies administered in Experiments 3 and 4, although much less than those of the non-depleting YTS177, were found previously to deplete animals of virtually all CD4+ or CD8+ T cells.

To ascertain the protective effect of YTS177 on islet morphology, cryostat sections were prepared from the pancreata of Experiment 3 mice and stained for infiltrating T cells. Examination of pancreata from untreated mice sacrificed at day 12 after transfer revealed that peri-islet infiltration was already extensive with some intra-islet lymphocytes also present although the number of residual islets was still relatively low (23%). Pancreata from animals given YTS177 from day 12 onwards and killed at 4 weeks after transfer were indistinguishable from the previous group (19% residual islets) suggesting that the antibody had arrested the infiltration and prevented any further β cell destruction.

In contrast, the animals given no antibody treatment and killed at week 4 had extensive intra-islet infiltration and 70% of the islets were residual. Group 5 (treated with depleting CD8 mAb from day 12 onwards) although not yet overtly diabetic, nevertheless displayed evidence of considerably more B cell destruction (51% residual islets) than the mice treated with YTS177. In Experiment 4, where animals similarly treated were allowed to go on beyond 4 weeks, it was seen that by 8 weeks, 3/5 of the Group 5 animals were diabetic whereas none of the YTS177 treated mice showed any signs of overt disease. In the same experiment it was seen that the depleting CD4 mAb afforded no significant or lasting protection.

It could be argued that YTS177 is effective simply as a result of general immunosuppression, but when SRBC were administered i.p. to Group 4 mice two weeks after cessation of YTS177 treatment, or to a group of NOD mice irradiated and reconstituted with $2 \times 10^7$ normal spleen cells, the level of agglutinating anti-SRBC antibody found in the sera 5 days later, were comparable in both groups.

The protection afforded by antibody YTS177 was unexpectedly powerful when compared with the effect of monoclonal antibodies depleting either of the two major T cell subsets. In the case of the latter, it may be expected that newly emerging T cells will eventually be able to mount a response against β cells and any protection would thus be of limited duration. The nd CD4 mAb, by switching off β cell specific effectors and, perhaps, by initiating a protective idiotypic network, seems to offer permanent protection.

TABLE 1

| | | Number of mice diabetic at week 4 or 5 after transfer | | | | |
|---|---|---|---|---|---|---|
| Exp No | Group 1 (Control) | Group 2 (nd CD4 mAb d 0-30) | Group 3 (nd CD4 mAb d 0-10) | Group 4 (nd CD4 mAb d 12+) | Group 5 (d CD8 mAb d 12+) | Group 6 (d CD4 mAb d 12+) |
| 1 | 4/5 | 0/4 | 0/4 | N.D. | N.D. | N.D. |
| 2 | 3/4 | 0/4 | N.D. | 0/5 | N.D. | N.D. |
| 3 | 4/4 | N.D. | N.D. | 0/5 | 0/5 | N.D. |
| 4 | 2/5 | N.D. | N.D. | 0/4 | 1/5 | 2/4 |
| Total | 13/18 | 0/8 | 0/4 | 0/14 | 1/10 | 2/4 |

We claim:

1. A method of arresting the loss of insulin-producing cells in a host subject to such loss which comprises administering to the host an effective amount administered being sufficient CD4 monoclonal antibody the amount administered being sufficient to arrest the loss of insulin-producing cells.

2. The method of claim 1 for treating insulin-dependent diabetes mellitus.

3. The method of claim 1 for protecting the host's β-cells.

4. The method claim 1 for permitting regeneration of the host's β-cells.

5. The method of claim 1 which comprises administering more than one dose of non-depleting CD4 monoclonal antibodies.

6. The method of claim 1 herein the treatment is free from the administration of any depleting antibodies and any CD8 antibodies.

7. The method of claim 1 wherein the administration comprises the use of a saturating amount of at least one non-depleting CD4 monoclonal antibody.

8. A method of treatment of insulin dependent diabetes mellitus which method comprises administering to a patient in need thereof an effective, non-toxic amount of at least one non-depleting CD4 monoclonal antibody.

9. The method of claim 1 wherein the monoclonal antibody is YTS 177.9 produced by hybridoma ECACC 90053005.

* * * * *

UNITED STATES PATENT AND TRADEMARK OFFICE
CERTIFICATE OF CORRECTION

PATENT NO. : 5,670,150
DATED : September 23, 1997
INVENTOR(S) : Cooke et al.

It is certified that error appears in the above-identified patent and that said Letters Patent is hereby corrected as shown below:

THE TITLE PAGE

After "[63] Continuation of Ser. No. 90,203, Dec. 1, 1993, abandoned" insert --, filed as PCT/GB92/00074, January 14, 1992, abandoned--.

Signed and Sealed this

First Day of August, 2000

Attest:

Attesting Officer

Q. TODD DICKINSON

Director of Patents and Trademarks